(12) United States Patent
Carpenter et al.

(10) Patent No.: US 11,975,162 B2
(45) Date of Patent: May 7, 2024

(54) METHOD AND APPARATUS FOR DELIVERY OF CELL THERAPIES

(71) Applicant: Stemplant, LLC, Camden, NJ (US)

(72) Inventors: Judith Carpenter, Moorestown, NJ (US); Jeffrey Carpenter, Moorestown, NJ (US); Spencer Brown, Mt Laurel, NJ (US)

(73) Assignee: STEMPLANT, LLC, Camden, NJ (US)

( * ) Notice: Subject to any disclaimer, the term of this patent is extended or adjusted under 35 U.S.C. 154(b) by 506 days.

(21) Appl. No.: 17/350,554

(22) Filed: Jun. 17, 2021

(65) Prior Publication Data

US 2021/0379343 A1 Dec. 9, 2021

Related U.S. Application Data

(63) Continuation of application No. 16/337,962, filed as application No. PCT/US2017/000073 on Nov. 2, 2017, now Pat. No. 11,116,945.

(60) Provisional application No. 62/416,189, filed on Nov. 2, 2016.

(51) Int. Cl.
*A61M 25/10* (2013.01)

(52) U.S. Cl.
CPC ...... *A61M 25/1002* (2013.01); *A61M 25/104* (2013.01); *A61M 2025/105* (2013.01); *A61M 2025/1086* (2013.01); *A61M 2202/0437* (2013.01)

(58) Field of Classification Search
CPC ............ A61M 25/1002; A61M 25/104; A61M 2025/105; A61M 2025/1086; A61M 2025/1013; A61M 25/10181; A61M 25/1009; A61M 2025/1063; A61M 2025/1097; A61M 25/007; A61M 2025/0058; A61M 2025/0093; A61M 37/0015; A61M 2037/0023; A61M 2037/003; A61M 2037/0038; A61M 2037/0046; A61M 2037/0053; A61M 2037/0061; A61M 2025/0085; A61M 2025/0087; A61M 2202/0437; A61M 2025/109; A61B 17/22; A61B 2017/22051; A61B 2017/22081; A61B 2017/22084

See application file for complete search history.

(56) References Cited

U.S. PATENT DOCUMENTS

| | | |
|---|---|---|
| 5,087,244 A | 2/1992 | Wolinsky et al. |
| 5,370,617 A | 12/1994 | Sahota |
| 5,616,149 A | 4/1997 | Barath |

(Continued)

FOREIGN PATENT DOCUMENTS

| | | |
|---|---|---|
| CN | 102740800 | 10/2012 |
| EP | 0783898 | 7/1997 |

(Continued)

OTHER PUBLICATIONS

Office Action for IL 266364 dated Dec. 19, 2021.

(Continued)

*Primary Examiner* — Jason E Flick
(74) *Attorney, Agent, or Firm* — BakerHostetler

(57) ABSTRACT

A method and apparatus for delivery of cell therapies, introduced via percutaneous access to the circulation, and delivered to the site of vascular injury intervention.

20 Claims, 1 Drawing Sheet

(56) References Cited

U.S. PATENT DOCUMENTS

| | | | |
|---|---|---|---|
| 5,681,281 A * | 10/1997 | Vigil | A61M 25/10 604/103.01 |
| 5,921,954 A | 7/1999 | Mohr, Jr. et al. | |
| 5,985,307 A | 11/1999 | Hanson et al. | |
| 6,656,155 B2 | 12/2003 | Freyman | |
| 7,985,200 B2 | 7/2011 | Lary et al. | |
| 8,691,216 B2 | 4/2014 | Fraser et al. | |
| 8,696,621 B2 | 4/2014 | Gunday et al. | |
| 9,198,937 B2 | 12/2015 | Fraser et al. | |
| 10,213,579 B2 | 2/2019 | Alt | |
| 11,116,945 B2 | 9/2021 | Carpenter et al. | |
| 2003/0114793 A1 * | 6/2003 | Freyman | A61M 25/1002 604/509 |
| 2003/0181887 A1 | 9/2003 | Castillo Deniega et al. | |
| 2004/0064093 A1 | 4/2004 | Hektner et al. | |
| 2006/0008449 A1 * | 1/2006 | Van Tassel | A61B 17/3478 435/366 |
| 2006/0058815 A1 | 3/2006 | Mickley et al. | |
| 2007/0250035 A1 | 10/2007 | El-Nounou et al. | |
| 2008/0058763 A1 | 3/2008 | Boland et al. | |
| 2010/0069837 A1 | 3/2010 | Rasset et al. | |
| 2011/0166516 A1 | 7/2011 | Orr | |
| 2011/0301571 A1 | 12/2011 | Guimaraes | |
| 2012/0289982 A1 | 11/2012 | Gunday et al. | |
| 2014/0058358 A1 | 2/2014 | Kassab | |
| 2015/0094701 A1 | 4/2015 | Pageard | |
| 2016/0183963 A1 | 6/2016 | Richter et al. | |
| 2017/0080192 A1 | 3/2017 | Giasolli et al. | |
| 2020/0038637 A1 | 2/2020 | Carpenter et al. | |
| 2020/0197671 A1 | 6/2020 | Risch et al. | |
| 2021/0379343 A1 | 12/2021 | Carpenter et al. | |

FOREIGN PATENT DOCUMENTS

| | | |
|---|---|---|
| EP | 2407202 | 1/2012 |
| EP | 2692391 | 2/2014 |
| JP | H5-293176 A | 11/1993 |
| JP | 2005-532120 A | 10/2005 |
| JP | 2006-501869 A | 1/2006 |
| KR | 2012-0010658 A | 2/2012 |
| KR | 2013-0042541 A | 4/2013 |
| WO | WO 2002/043796 | 6/2002 |
| WO | WO2010/024871 | 3/2010 |
| WO | WO 2012/018899 | 2/2012 |

OTHER PUBLICATIONS

Office Action for JP 2019-545876 dated Mar. 28, 2022.
Office Action for CN 201780067683.4 dated Apr. 11, 2022.
Office Action for AU 2017355939 dated Jun. 16, 2022.
Inhibitory Effects of Mesenchymal Stem Cells in Intimal Hyperplasia After Balloon Angioplasty, Ae-Kyeong Kim, PhD, a Min-Hee Kim, a Do-Hyung Kim, a Ha-NI Go, a Seung-Woo Cho, PhD, b Soong Ho Um, PhD, c and Donglk Kim, MD, PHD, http://dx.doi.org/10.1016/j.jvs.2014.08.058.
International Search Report and Written Opinion for International Application No. PCT/US2017/000073 dated Apr. 13, 2018; 13 pages.
International Search Report and Written Opinion for International Application No. PCT/US2020/048832 dated Nov. 9, 2020; 14 pages.
Supplemental Partial European Search Report for EP 17867091 dated Sep. 16, 2020.
Extended European Search Report for EP 17867091 dated Dec. 22, 2020.
Office Action for CN 201780067683.4 dated Feb. 2, 2021.
Office Action for JP 2019-545876 dated Jun. 25, 2021.
Office Action for CN 201780067683.4 dated Jul. 12, 2021.

* cited by examiner

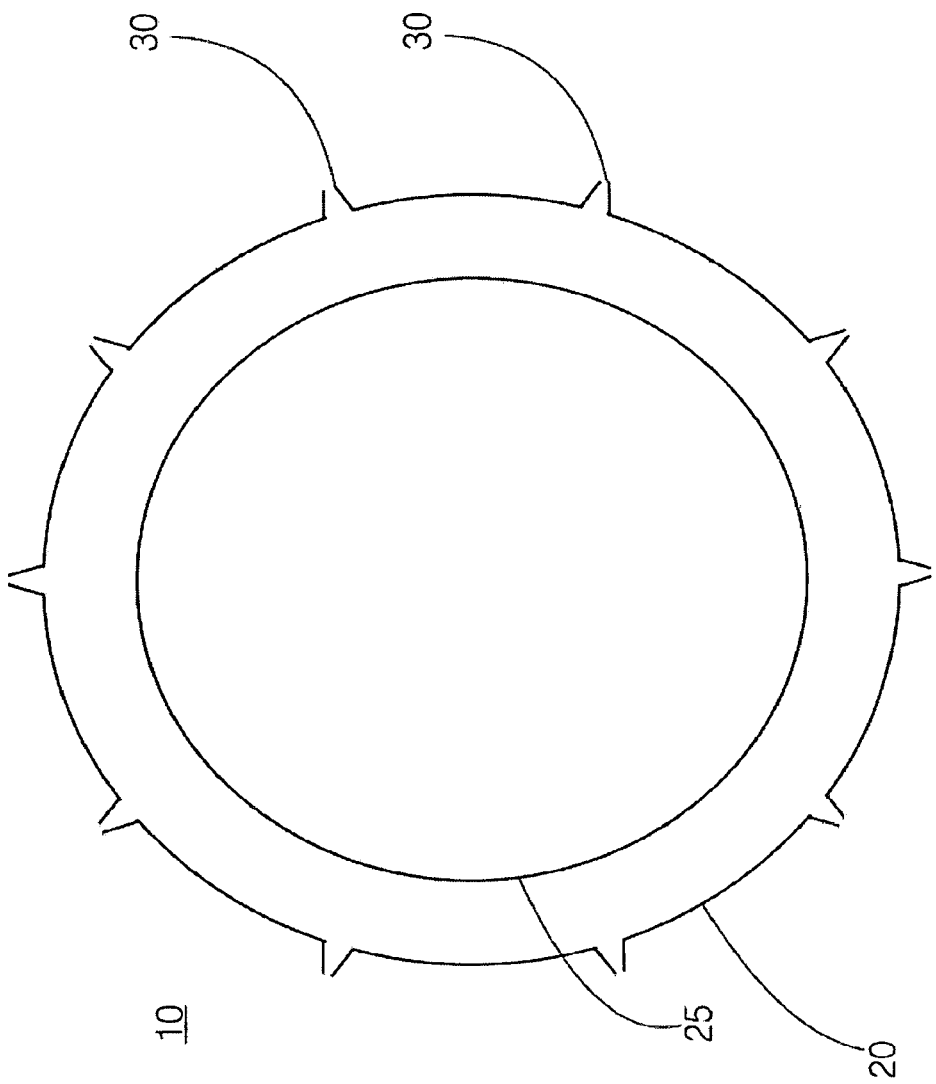

METHOD AND APPARATUS FOR DELIVERY OF CELL THERAPIES

This application is a continuation of U.S. patent application Ser. No. 16/337,962, filed on Mar. 29, 2019, which is a U.S. National Stage Application under 35 U.S.C. § 371 of International Patent Application No. PCT/US2017/000073, filed Nov. 2, 2017, which claims priority from U.S. Provisional Patent Application No. 62/416,189, filed Nov. 2, 2016. The entirety of each of the foregoing applications is hereby incorporated by reference herein.

BACKGROUND OF THE INVENTION

Cardiovascular disease is the leading cause of mortality worldwide. Atherosclerosis can lead to symptomatic blockages of major coronary arteries resulting in angina or myocardial infarction. The most common treatments include bypass surgery, atherectomy, and balloon angioplasty combined with implantation of stents. Intimal hyperplasia is the most common failure mode for atherectomy, angioplasty, and stenting. This major problem occurs after all percutaneous coronary interventions resulting in restenosis of the involved coronary arteries at rates as high as 15-30% within the first year. Intimal hyperplasia consists of an accumulation of vascular smooth muscle cells that migrate to the intimal space as well as a deposition of extracellular matrix material. The result is a decrease in the luminal diameter of the affected vessel with resultant ischemia of the end organ. The importance of treating the causes of intimal hyperplasia to prevent restenosis is evident in its prevalence and in the myriad of devices and treatments that have been proposed to address the problem.

The initial treatments involved attempts at preventing restenosis after angioplasty due to intimal hyperplasia by the development of stents. These treatments failed due to intimal hyperplasia growing through the holes in the stents. Covered stents were then developed to prevent this, but intimal hyperplasia developed at the ends of the covered stents causing restenosis. More recent treatments have attempted to address particular steps or factors in the process of intimal hyperplasia. Their lack of success can generally be attributed to the complex mechanisms involved in the development of intimal hyperplasia and to the difficulty in delivering effective treatment. The causes of intimal hyperplasia include hemodynamic factors such as shear stress and wall tensile stress, injury including endothelial denudation and medial tearing, inflammation, and genetic factors. Each of these causes involves complex pathways and a variety of cells and chemical mediators. Numerous drug therapies have been developed to attempt to decrease the development of intimal hyperplasia by targeting a specific step or cell in a particular pathway, or minimizing the initiating cause.

Current treatments to reduce intimal hyperplasia include the use of drug eluting stents and drug eluting angioplasty balloons. Some of these stents and balloons are coated with various drugs that transfer from the stent or balloon surface by direct contact with the site of the angioplasty or intervention. Others allow release of the drug near the vessel wall. The drug then contacts the vascular tissue and exerts its inhibitory effect 011 the hypertrophic scarring n:at:lion (intimal hyperplasia) with the goal of decreasing the likelihood of a recurrent blockage at the treatment site.

The prior art contains many examples of devices for delivery of drugs to blood vessels. Among these are U.S. Pat. No. 5,087,244 to Wolinsky, et al.; U.S. Pat. No. 5,985,307 to Hanson, et al.; and U.S. Pat. No. 7,985,200 to Lary, et al.

Another critical vascular disease state is ruptured aneurysms, which are a leading cause of death worldwide. At present, treatment is surgical excision or ablation; there is no medical therapy for prevention or arrest of this disease. The pathophysiology of aneurysm disease has been demonstrated to be arterial degeneration, having a significant inflammatory component. The inflammatory process is located in the arterial wall and the surrounding periadventitial fat and tissues.

The prior art of preparation and use of adipose-derived stem cells includes U.S. Pat. No. 8,691,216 to Fraser, et al., and U.S. Pat. No. 9,198,937 to Fraser, et al. in which such stem cells are used to promote wound healing and liver injury by delivery via a catheter equipped with a balloon.

Recently it has been shown that intimal hyperplasia can be reduced by the introduction of stem cells to the site of angioplasty-induced arterial injury from outside the vessel. (*Inhibitory Effects of Mesenchymal Stem Cells in Intimal Hyperplasia After Balloon Angioplasty*, Ae-Kyeong Kim, PhD, a Min-Hee Kim, a Do-Hyung Kim, a Ha-Nl Go, a Seung-Woo Cho, PhD, b Soong Ho Urn, PhD, c and Dong-Ik Kim, MD, PhD.

It is also believed that stem cell therapies may be a candidate medical therapy for aneurysms. No delivery systems for cellular therapies are currently available or appropriate for treatment of aneurysm disease. The fragility of the affected arterial wall presents special challenges for delivery of therapies with the risk of manipulation of the aneurysmal tissue at the time of treatment.

Finally, it is believed that stem cell therapies may be used as medical treatments for other disease states, provided that cellular suspensions may be delivered directly in close proximity to the tissue needing treatment, and delivery via the circulatory system using percutaneous access is a desired method.

Devices for delivery of cell therapies to the lumen of the vessel for this type of application have not been developed or commercialized. A difference between current drug-coated interventional devices and cell therapies is that to be viable, stem cells must be freshly prepared and maintained in suspension (as opposed to coated on the interventional apparatus and maintained in a dry state for storage). A further difference is that stem cells (and other cellular suspensions) are larger in size compared to drug molecules, and would be swept away from the interventional site by blood flowing though the vessel after the procedure is completed. Thus, a new method of delivering a liquid suspension of properly prepared fresh stem cells or non-stem cells to the site of the intervention, and retaining them there is required.

BRIEF DESCRIPTION OF THE INVENTION

The disclosed invention is a method and apparatus for delivery of cell therapies, introduced via percutaneous access to the circulation, and delivered to the site of vascular injury or intervention or to the surrounding tissue. The cellular suspensions are delivered to the intima, subintimal space, media, adventitia, or periadventitial space from within the lumen of the vessel or to periarterial tissues and fat from within the lumen of an adjacent vessel.

BRIEF DESCRIPTION OF THE FIGURE

FIG. 1 depicts a cross-section view of an embodiment of the delivery device of the present invention.

DETAILED DESCRIPTION OF THE INVENTION

A preferred embodiment of the present invention is a balloon that carries on its surface one or more tubes having apertures or a continuous groove. Once inflated to fracture the plaque layer, the cellular suspension is introduced through the tube where it flows from the apertures (or groove) into the vessel wall. This embodiment may be equipped with a central passage to permit blood flow during inflation. The medium in which the cells are suspended may be a biologically neutral or active solution, and may optionally comprise drugs, biological agents, and other additives.

The delivery device of the present invention illustrated in FIG. 1 is a toroidal balloon (10), having hollow rigid spikes (30) on its outer surface (20). This balloon is attached to a conventional catheter (not shown) for percutaneous access to a vessel under treatment and is positioned in the vessel in an uninflated or minimally inflated state. The inner wall (25) of the toroidal balloon may be made of relatively stiff material to facilitate insertion and placement of the balloon. Once in place, the balloon may be inflated by the introduction of a cellular suspension under pressure, which both inflates the balloon (10), drives the hollow rigid spikes (30) into and through the plaque layer, and delivers the suspension through the spikes (30) into the plaque and/or the desired structure of the vessel wall. The balloon (10) is then deflated and withdrawn, leaving the stem cells behind, but protected from being swept away in the blood flow. Because the balloon (10) is toroidal, blood flow through the vessel under treatment is never interrupted.

In an alternative embodiment (not shown), balloon (10) may be spherical or elongated, but not toroidal, and during inflation, will interrupt blood flow through the vessel under treatment. Balloon (10) may optionally be provided with annular flanges (not shown) at the proximal and distal ends. These flanges engage the vessel wall, and serve to prevent blood flow between the vessel wall and the outer surface (20), instead directing blood flow through the torus.

The method of the present invention for treatment of intimal hyperplasia requires that the plaque layer within the vessel to be treated be either fractured or penetrated, and that a suspension of stem or non-stem cells be delivered beneath the plaque to the intima, subintimal space, media, adventitia, and/or periadventitial space. The fracturing of the plaque may be by inflation of a balloon, as is common in angioplasty, or by other mechanical means, such as the compression of a stent-like device to increase its diameter after positioning in the vessel. The fracturing of the plaque may be by conventional means, such as inflation of a balloon, prior to and separate from the introduction of stem cells according to the present invention, or may be combined in a single device which both fractures the plaque and subsequently introduces the cellular suspension. Penetration of the plaque may be by extension of spikes or similar structures after positioning a delivery device of the present invention within the vessel. In either case, after fracturing or penetration, a suspension of stem cells is delivered under sufficient pressure to move the cells into the plaque layer and/or one or more of the selected structural layers of the vessel under treatment, where they remain after removal of the delivery device.

Another alternative embodiment of the delivery device of the present invention (not shown) is a helical or double-helical arrangement of thin tubes having small apertures at intervals along the length of the tubes. Similar in appearance to a conventional stent, the device is inserted into a vessel using a catheter and positioned as desired. It is then drawn together to increase its diameter (by movement of a conic member, not shown), thereby being used to fracture the plaque layer and become deeply embedded in the plaque. Alternatively, the device may be formed from a memory metal which expands when freed from a constraining sheath, or when heated to body temperature. The catheter is then used to introduce a cell-based suspension to the tubes and this suspension exits the tubes through the small apertures. After introduction of the stem cells, the device is elongated to reduce its diameter, disengage it from the vessel wall, and it is withdrawn along with the catheter.

Yet another embodiment is a multi-lobed balloon, having small apertures or hollow spikes at the apex of each lobe where it contacts the vessel wall.

Yet another embodiment is a multi-lobed balloon, having one or more apertures within the space between the lobes, which space defines a channel that may be filled with a cellular suspension, to provide increased area of contact between the plaque layer and the suspension. In this embodiment, annular flanges, as described above, are used to contain the cellular suspension, and to direct blood flow through a central hollow lumen in the balloon, or through alternate channels on the outer surface of the balloon, in which case the annular flanges have apertures or notches that communicate with such channels or the central lumen.

Each balloon described above may, of course, be of double-lumen design to allow inflation using a fluid that is separate and distinct from the cellular suspension to be delivered to the vessel wall.

For interventions directed to aneurysm therapy, the previously-described cell suspension delivery systems capable of fully penetrating the venous wall may be used for delivery of cell therapy into the surrounding periarterial tissues and fat rather than directly into the aneurysmal arterial wall. Most arteries are adjacent to a paired vein. The cell suspension delivery device is inserted via the adjacent vein and deployed in the vein. When deployed, hollow spikes on the device penetrate through the venous wall into the tissue surrounding the aneurysmal artery. The cell preparation is delivered through the spikes after which the device is retrieved and removed. Alternatively, the cell preparation may be delivered via a catheter which is directed to contact and provide support against the venous wall. Once in contact with the wall, one or more needles, or spikes can be deployed and the injection delivered into the periarterial tissues.

While the invention has been described in its preferred embodiments, it is to be understood that the words which have been used are words of description rather than of limitation and that changes may be made within the purview of the appended claims without departing from the true scope and spirit of the invention in its broader aspects. Rather, various modifications may be made in the details within the scope and range of equivalents of the claims and without departing from the spirit of the invention. The inventors further require that the scope accorded their claims be in accordance with the broadest possible construction available under the law as it exists on the date of filing hereof (and of the application from which this application obtains priority, if any) and that no narrowing of the scope of the appended claims be allowed due to subsequent changes in the law, as such a narrowing would constitute an ex post facto adjudication, and a taking without due process or just compensation.

We claim:

1. A method for treatment of arterial degeneration comprising:

introducing a delivery device to a lumen of an artery with aneurysm disease due to inflammation located in an arterial wall and surrounding periarterial fat and tissues, and positioning the delivery device in close proximity to the arterial wall;

mechanically penetrating the arterial wall into the periarterial fat and tissues to be treated;

delivering, under pressure, a quantity of stem cells in suspension through the delivery device into the periarterial fat and tissues, wherein the quantity of stem cells in suspension penetrates the arterial wall;

wherein the quantity of stem cells in suspension remain within the periarterial fat and tissues to treat the aneurysm disease.

2. The method of treatment of claim 1, wherein mechanically penetrating the arterial wall comprises inflating a balloon.

3. The method of treatment of claim 1, wherein delivering, under pressure, the quantity of stem cells comprises delivering the quantity of stem cells to an intima, subintimal space, media, adventitia, or periadventitial space.

4. The method of treatment of claim 1, wherein introducing the delivery device to the lumen of the artery comprises positioning one or more tubes having a groove.

5. The method of treatment of claim 1, wherein introducing the delivery device to the lumen of the artery comprises permitting blood flow through the artery.

6. The method of treatment of claim 1, wherein introducing the delivery device to the lumen of the artery comprises interrupting blood flow.

7. The method of treatment of claim 1, wherein delivering, under pressure, the quantity of stem cells comprises delivering drugs into the periarterial fat and tissues.

8. The method of treatment of claim 1, further comprising preparing the stem cells in suspension.

9. The method of treatment of claim 1, wherein introducing the delivery device to the lumen of the artery comprises percutaneous access.

10. The method of treatment of claim 1, wherein delivering, under pressure, the quantity of stem cells comprises penetration of the arterial wall with a needle.

11. The method of treatment of claim 1, further comprising introducing the delivery device to a lumen of a paired vein.

12. The method of treatment of claim 11, further comprising mechanically penetrating a venous wall of the paired vein.

13. The method of treatment of claim 12, further comprising delivering, under pressure, a quantity of stem cells in suspension through the delivery device into the periarterial fat and tissues, wherein the quantity of stem cells in suspension penetrates the venous wall.

14. A method for treatment of arterial degeneration comprising:

introducing a delivery device to a lumen of a paired vein of an artery with aneurysm disease due to inflammation located in an arterial wall and surrounding periarterial fat and tissues, and positioning the delivery device in close proximity to a venous wall of the paired vein;

mechanically penetrating the venous wall into the periarterial fat and tissues to be treated;

delivering, under pressure, a quantity of stem cells in suspension through the delivery device into the periarterial fat and tissues, wherein the quantity of stem cells in suspension penetrates the venous wall;

wherein stem cells in suspension remain within the periarterial fat and tissues to treat the aneurysm disease.

15. The method of treatment of claim 14, wherein mechanically penetrating the venous wall comprises inflating a balloon.

16. The method of treatment of claim 14, wherein delivering, under pressure, the quantity of stem cells comprises delivering the quantity of stem cells to an intima, subintimal space, media, adventitia, or periadventitial space.

17. The method of treatment of claim 14, wherein delivering, under pressure, the quantity of stem cells comprises delivering drugs into the periarterial fat and tissues.

18. The method of treatment of claim 14, further comprising preparing the stem cells in suspension.

19. The method of treatment of claim 14, wherein introducing the delivery device to the lumen of the paired vein comprises percutaneous access.

20. The method of treatment of claim 14, wherein delivering, under pressure, the quantity of stem cells comprises penetration of the venous wall with a needle.

* * * * *